(12) United States Patent
Theeuwes et al.

(10) Patent No.: US 6,726,920 B1
(45) Date of Patent: Apr. 27, 2004

(54) IMPLANTABLE DRUG DELIVERY PATCH

(75) Inventors: Felix Theeuwes, Los Altos Hills, CA (US); Timothy S. Nelson, Los Gatos, CA (US)

(73) Assignee: Durect Corporation, Cupertino, CA (US)

( * ) Notice: Subject to any disclaimer, the term of this patent is extended or adjusted under 35 U.S.C. 154(b) by 0 days.

(21) Appl. No.: 09/668,684

(22) Filed: Sep. 22, 2000

(51) Int. Cl.[7] .................... A61F 2/02; A61F 13/02; A61L 15/16; A61K 9/70; A61N 1/30
(52) U.S. Cl. .................. 424/423; 424/422; 424/424; 424/425; 424/426; 424/447; 424/448; 424/449; 604/19
(58) Field of Search ................ 424/422, 423, 424/424, 425, 426, 447, 448, 449; 604/19

(56) References Cited

U.S. PATENT DOCUMENTS

| | | | |
|---|---|---|---|
| 4,597,961 A | | 7/1986 | Etscorn |
| 5,071,656 A | * | 12/1991 | Lee et al. .............. 424/448 |
| 5,087,243 A | * | 2/1992 | Avitall .................. 604/20 |
| 5,387,419 A | * | 2/1995 | Levy et al. ............ 424/422 |
| 5,634,895 A | | 6/1997 | Igo et al. |
| 5,827,216 A | | 10/1998 | Igo et al. |
| 5,931,810 A | | 8/1999 | Grabek |
| 5,972,013 A | | 10/1999 | Schmidt |

FOREIGN PATENT DOCUMENTS

| EP | 0 153 200 | 8/1985 |
|---|---|---|
| WO | WO 98/31315 | 7/1998 |

* cited by examiner

Primary Examiner—Carlos A. Azpuru
(74) Attorney, Agent, or Firm—Adam W. Bell (57) ABSTRACT

The present invention features devices and methods for delivery of drug to an internal organ surface by delivery of drug directly to the surface of the organ such that the drug traverses the organ surface and enters the organ tissue. The device is in the form of an implantable drug delivery patch comprising a first layer, which is generally substantially drug-impermeable. When the first layer is placed on an outer surface of an organ, a drug reservoir is defined by the first layer and the organ surface.

33 Claims, 6 Drawing Sheets

IMPLANTABLE DRUG DELIVERY PATCH

FIELD OF THE INVENTION

The present invention relates generally to the field of site-specific drug delivery, particularly to delivery of drugs to a target organ.

BACKGROUND OF THE INVENTION

Delivery of drug to a specific treatment site represents a substantial challenge in the design of drug delivery systems. While drugs designed for action at or within a specific organ (e.g., the heart, liver, pancreas, prostate, and the like) may be suitable for systemic delivery, the amount of drug that must be delivered by this route generally must be quite high in order to result in delivery of a therapeutically effective amount at the desired site of action. Delivery of such high amounts of drug increases the likelihood and severity of side effects, and is otherwise disadvantageous, e.g., in terms of cost-effectiveness of therapy. One approach to accomplish site-specific drug delivery involves the use of a catheter, which can be positioned at a treatment site to facilitate localized delivery of drug from a drug reservoir of a drug device (e.g., an external or implanted pump) that may be positioned some distance from the treatment site. However, delivery of agents to a site within an organ generally requires breaking the surface of the organ to implant a catheter tip within the organ. This may be particularly undesirable where the organ is sensitive or already damaged, and may compromise the integrity of structures surrounding the organ.

The heart is an example of an organ of particular interest for organ-specific delivery. The pericardium, or pericardial sac, is a membranous sac in which the heart is contained. The pericardium and the pericardial fluid together function to prevent dilation of the chambers of the heart, to lubricate the surfaces of the heart, and to maintain the heart in a fixed geometric position. The space between the pericardium and the heart, known as the pericardial space, contains the pericardial fluid which bathes the heart.

Delivery of therapeutic agents directly to the pericardial space for treating various cardiac disorders overcomes some of the disadvantages associated with systemic delivery of these agents. For example, systemic dosages sufficient to confer a therapeutic effect on the heart may produce undesired side effects on other organs and tissues of the body. Current methods for accessing the pericardial space require puncturing the pericardial sac to introduce a needle or a catheter. See, for example, U.S. Pat. Nos. 5,931,810; and 5,827,216. Others means of accessing the pericardial space involve the use of an iontophoretic device. See, for example, U.S. Pat. No. 5,634,895. Each of these devices carries with it inherent risks to the pericardium and/or the heart muscle, such as puncturing or mechanically damaging the cardiac tissue, or inducing fibrillation upon application of an electric field.

U.S. Pat. No. 5,387,419 states that a biocompatible polymeric matrix with an incorporated anti-arrhythmic agent can be applied directly to the heart muscle via the epicardium, endocardium, or pericardium. This matrix has limitations in that the drug to be delivered must be integrated into a polymer to form a biocompatible matrix which requires the steps of forming a mixture of the drug and polymer, forming the mixture into a desired shape and curing formed mixture for a period of time. The foregoing steps may be difficult, time consuming and/or require use of catalytic chemicals or high pressure. Furthermore, because the device requires that the drug must be integrated into the polymer, this may limit drug loading (i.e., the amount of drug that can be incorporated into the polymer) which in turn limits the duration and dose of the drug that can be delivered, and in addition, requires that the drug and polymer to be compatible with each other (i.e., drug and polymer must be miscible and not adversely reactive to each other). In addition, because the device requires drug to be integrated into a polymer, it may be relatively more difficult to replenish the drug contained in the patch once such patch is attached to the heart where prolonged delivery of a drug is required (e.g., for the treatment of a chronic disease).

There is a need in the art for improved devices and methods for delivering therapeutic agents directly to or into an organ of interest. The present invention addresses this need by providing an implantable drug delivery patch and drug delivery system.

SUMMARY OF THE INVENTION

The present invention features devices and methods for delivery of drug to or into an internal organ by delivery of drug directly to the surface of the organ such that the drug traverses the organ surface and enters the organ tissue. The device is in the form of an implantable drug delivery patch comprising a first layer, which is generally substantially drug-impermeable. When the first layer is placed on an outer surface of an organ, a drug reservoir is defined by the first layer and the organ surface.

In some embodiments, the patch further comprises a second layer, which, when the patch is placed onto an outer surface of an organ, is disposed between the organ surface and the first layer. In these embodiments, the second layer comprises a drug-permeable membrane, and a drug reservoir is defined by the first layer and the drug-permeable membrane of the second layer.

The patch is held in place on the organ surface with an attachment element, which can be part of the first layer or, if present, the second layer, or can be a separate component which is attached to the first layer or the second layer, and is adjacent the delivery surface.

The patch is useful for delivering a wide variety of therapeutic agents and thus is useful in treating various conditions, and is also useful for systemic delivery of a therapeutic agent. The implantable drug delivery patch of the invention is advantageous in that the drug can be delivered to the organ without disrupting or compromising any organ structure, e.g., by puncturing or subjecting to an electrical field. The patch of the invention can also be used in patients who do not have organs with intact sacs surounding the organ to which drug is to be delivered.

In some embodiments, the patch of the invention is refillable. In some of these embodiments, refilling is achieved by accessing the patch with a catheter or a needle which provides a conduit from a drug delivery device or a drug source at a distal site. Thus, an advantage of this embodiment of the drug delivery patch of the invention is that it can be refilled. The refillable feature of the patch confers a number of advantages in that the need to replace the patch is avoided; the volume rate of delivery can be controlled; and the concentration gradient of the drug across the organ surface can be maintained.

A further advantage of the patch of the invention is conferred by the first layer, which, in those embodiments in which the first layer is substantially impermeable to body fluids, protects the drug contained in the reservoir from interaction with body fluids outside the organ. This is particularly advantageous when drugs that are sensitive to molecules in body fluids, such as enzymes, are being delivered. In addition to protecting the drug from degradation, the first layer can also be made to be drug-impermeable, so as to prevent or reduce dilution of the drug contained within the reservoir, and may limit drug loss to the environment surrounding the target organ.

A further advantage is that the patch of the invention may further comprise a second layer comprising a material having properties that allow a controlled drug delivery rate, thus providing better dosing control.

The invention further provides a drug delivery system comprising a patch of the invention, a catheter, and a distal drug delivery device. The drug delivery device may be a convective delivery device, e.g., suitable for low volume rate delivery.

Another advantage of the invention is that the effective dose of drug can be lower since drug is delivered to a localized, or regional, treatment site at the organ of interest, thus avoiding or mitigating the adverse side effects of such drugs when administered systemically in doses sufficient to be efficacious.

A further advantage of the invention is that the patch can be adapted for consistent, continuous, dosing of a therapeutic agent.

These and other objects, advantages, and features of the invention will become apparent to those persons skilled in the art upon reading the details of the invention as more fully described below.

BRIEF DESCRIPTION OF THE DRAWINGS

FIGS. 2A and 2B are cut-away views; FIGS. 2C and 2D are views from the drug delivery side of the patch.

DETAILED DESCRIPTION OF THE INVENTION

The present invention provides an implantable drug delivery patch useful for delivering a therapeutic or diagnostic agent to a target organ or into the target organ tissue. The patch comprises a first layer which generally comprises materials that are substantially drug-impermeable. The patch is placed on an outer surface of the target organ. In these embodiments, the first layer forms a drug reservoir between the first layer and an outer surface of the target organ.

In some embodiments, the drug delivery patch of the invention further comprises a second layer, interspersed between the first layer and the outer surface of the target organ. In these embodiments, a drug reservoir is defined by the first layer and the second layer. The second layer comprises a drug-permeable portion. The drug-permeable portion of the second layer is adjacent to the outer surface of the organ, and allows the drug to exit the reservoir and contact the organ outer surface. The drug-permeable portion of the second layer may be in direct physical contact with the outer surface of the organ, or there may be a small space between the drug-permeable portion and the organ outer surface.

The patch is affixed to the organ surface by an attachment element, which may be an adhesive portion of the first layer, or, if present, the second layer, or, alternatively, by an attachment element that is a separate component which is attached to the first layer or the second layer.

The drug in the reservoir traverses the organ surface, enters any fluid that may be present between the organ outer surface and the organ tissue, and subsequently into the organ tissue. The drug reservoir of the patch can be accessed by means of a catheter or syringe after affixing the patch to the organ surface, thereby allowing the clinician to refill the reservoir, and to control the rate of delivery. The patch may also be part of a drug delivery system, comprising the patch, a catheter, and a drug delivery device, which may be an implantable device.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a drug" includes a plurality of drugs and reference to "the device" includes reference to one or more devices and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The terms "subject," "individual," and "patient," used interchangeably herein, refer to any subject, generally a mammal (e.g., human, canine, feline, equine, bovine, rodent, etc.), in which delivery to or into an organ is desired.

"Organ" or "target organ" as used herein is meant to refer to any internal organ to or into which site-specific drug delivery is desired.

The term "therapeutically effective amount" is meant an amount of a therapeutic agent, or a rate of delivery of a therapeutic agent, effective to facilitate a desired therapeutic effect.

As used herein, the terms "treatment", "treating", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

"Drug delivery device" as used herein is meant to encompass any device that can retain a quantity of drug and that facilitates movement of drug from the drug delivery device to a site external to the drug delivery device. "Drug delivery device" thus encompasses controlled drug release devices, as well as devices that release drug in an unpatterned (e.g., substantially unregulated) manner.

"Controlled release" as used herein (e.g., in the context of "controlled drug release") is meant to encompass release of substance (e.g., a drug) at a selected or otherwise controllable rate, interval, and/or amount. "Controlled release" thus encompasses, but is not necessarily limited to, substantially continuous delivery, patterned delivery (e.g., intermittent delivery over a period of time that is interrupted by regular or irregular time intervals), and delivery of a bolus of a selected substance (e.g., as a pre-determined, discrete amount of a substance over a relatively short period of time (e.g., a few seconds or minutes).

The term "controlled drug release device" is meant to encompass any device that provides for release (e.g., rate, timing, etc.) of a drug or substance contained therein at a rate that is controlled by or determined by the device itself and not the environment of use.

The term "low volume rate drug delivery" as used herein generally refers to delivery of a liquid or semisolid drug at a volume rate of from about 0.01 $\mu$l/day to about 200 $\mu$l/day, usually about 0.04 $\mu$l/day to about 20 $\mu$l/day, more usually about 0.1 $\mu$l/day to about 8.0 $\mu$l/day.

The term "substantially impermeable," as used herein in reference to patch material, refers to material that is sufficiently impermeable to a substance, e.g., a drug, body fluid, etc., such that there is substantially no migration of the substance into or out of the patch through the impermeable layer or other impermeable portion.

The terms "bioerodable" and "biodegradable" are used interchangeably herein to refer to a material that is dissolvable in physiological conditions by physiological enzymes and/or chemical conditions.

The terms "drug formulation," "formulation," and "drug," used interchangeably herein, are meant to encompass any substance suitable for delivery to an organ of a subject, which substances can include pharmaceutically active drugs, as well as biocompatible substances that do not exhibit a pharmaceutical activity in and of themselves, but that provide for a desired effect at a treatment site, e.g., to flush or irrigate a treatment site (e.g., saline).

The term "condition," as used herein, refers to any abnormal or pathological condition, particularly one associated with an organ to which drug delivery can be accomplished using an implantable patch of the invention. Exemplary conditions include, but are not necessarily limited to, microbial infection; ischemic disease; inflammation; myocardial infarction; thrombosis; and the like. Where the organ is the heart, exemplary cardiac conditions further include, but are not necessarily limited to, cardiac arrhythmia; cardiomyopathy; coronary angioplasty restenosis; congestive heart failure; cardiac atherosclerosis of a coronary artery cardiac tamponade; pericardial effusion; a cardiac condition related to hypertension; cardiac neoplasm; and cardiac inflammatory conditions such as endocarditis, pericarditis, and myocarditis.

The term "cardiac drug," as used herein, refers to any pharmaceutically active agent used to treat any cardiac condition, and includes, but is not limited to, growth factors, polynucleotides encoding growth factors, angiogenic agents, calcium channel blockers, antihypertensive agents, antimitotic agents, inotropic agents, antiatherogenic agents, anticoagulants, $\beta$-blockers, anti-arrhythmic agents, antiinflammatory agents, vasodilators, thrombolytic agents, cardiac glycosides, antibiotics, antiviral agents, antifungal agents, agents that inhibit protozoans, angiotensin converting enzyme (ACE) inhibitors; brain natriuretic peptide (BNP); antineoplastic agents, and steroids.

"Transorgan delivery" or "drug delivery" as used in the context of the present invention, is meant to encompass delivery of drug to the outer surface of an organ. In general, drug delivery according to the invention is accomplished by delivering drug from an implantable patch to tissue covering the organ outer surface, which is generally followed by delivery of drug to other organ tissue and fluids surrounding or contained within the organ. For example, a drug delivered to the outer surface of the heart can cross the pericardium, enters the pericardial fluid, traverses the epicardium and enters cardiac tissue.

The term "proximal end" (or "first end") is used herein in connection with components and/or structures which are closer to a clinician or other individual who is using a drug delivery system of the invention in a medical treatment setting. Conversely, the term "distal end" (or "second end") is used herein in connection with components and/or-structures which are closer to the treatment site or sampling site within the body of the subject being treated.

Overview

The invention relates to an implantable patch adapted for delivery of drug across the outer surface of an organ. In general, the patch comprises a first layer comprising a biocompatible material, which is generally substantially drug-impermeable. The patch is placed in contact with a portion of an outer surface of an organ of an individual. When placed on the organ surface, the first layer and organ surface form a drug reservoir, with the drug formulation in the reservoir in contact with the organ surface. Drug in the reservoir traverses the tissue of the organ surface to enter the tissue of the organ.

In some embodiments, the implantable drug delivery patch further comprises a second layer in contact with the first layer, the second layer comprising a drug-permeable portion. In these embodiments, a drug reservoir is defined by the first and second layers. The drug-permeable portion of the second layer is adjacent to the organ outer surface. Drug exits the reservoir through the drug-permeable portion of the second layer, traverses the organ outer surface, and enters the organ tissue. In some embodiments, and depending at least in part on the organ to which drug is delivered, drug may further enter the systemic circulation from the target organ.

The patch is affixed to the outer surface of the organ by an attachment element. The attachment element may be provided as an integral part of the first layer, or, if present, the second layer, or may be provided as a separate component which distinct from the second layer and which is affixed to the first layer or the second layer.

The invention further relates to a drug delivery system comprising an implantable patch according to the invention; a catheter having proximal and distal ends, the distal end being operably attached to the patch; and a drug delivery device operably attached to the proximal end of the catheter. The invention also provides methods of treating an individual comprising administering a drug via a drug delivery system which comprises a an implantable patch of the invention.

Implantable Patch

In general, the patch comprises a first layer (or "outer backing"). The patch is placed in contact with an outer surface of an organ. When in place on the organ surface, a reservoir is defined by the first layer and an outer surface of the organ. In general, the first layer is drug impermeable.

In some embodiments, the patch comprises a first layer and a second layer, which second layer comprises a drug-permeable membrane for rate-controlled delivery of drug, and a reservoir defined by the first and second layers.

The first layer, or, if present, the second layer, of the patch may further comprise an adhesive portion for holding the patch in place on the organ surface. Alternatively, a separate attachment element may be provided.

The patch may be composed entirely of biodegradable material, in which case the patch may be left in situ after use, e.g., after substantially all of the drug has exited the reservoir, or after delivery is discontinued. Alternatively, the patch may be removed from the body after use.

The patch can cover a discrete area of varying size over the organ surface. Alternatively, the patch can be in the form of a drug delivery sack, enveloping substantially all of the organ outer surface.

The specific aspects of the patch of the invention will now be described in further detail.

First Layer

The first layer is an outer backing layer and forms the portion of the patch that is at a distance away from the organ surface, e.g., is organ surface distal. In some embodiments, the first layer functions to provide an occlusive layer that is substantially drug impermeable, or alternatively, or in addition, substantially impermeable to body fluids and molecules. When substantially drug-impermeable, the first layer prevents loss of drug to the body through the substantially drug impermeable first layer. When the first layer is substantially impermeable to body fluids, the first layer prevents or reduces interaction between the drug and body fluids, which interaction may result in degradation or other undesired modification of the drug contained within the patch. In some embodiments, the first layer is drug permeable, and in other embodiments, the first layer is permeable to body fluids.

The first layer may comprise a portion which is raised (i.e, not flat, e.g., a hemisphere or a pouch) relative to the remainder of the first layer. When the first layer is placed in contact with an outer surface of the organ, this raised portion and the organ outer surface form a drug reservoir. In embodiments comprising a second layer, this raised portion (also referred to herein as the "reservoir portion" of the first layer) is arranged opposite the drug-permeable portion of the second layer, such that a drug reservoir is formed between the first and second layers, and particularly between a reservoir portion of the first layer and a drug-permeable portion of the second layer.

In some embodiments, the patch comprises a first layer and an attachment element, which are configured and positioned such that the patch envelops substantially all or a portion of the organ outer surface, e.g., the first layer can form a sack that substantially surrounds the organ. In one example of this embodiment, the attachment element is generally annular, and forms a seal such that a reservoir is formed between the first layer and the organ outer surface.

The first layer may further comprise an access port through which additional drug formulation can be added to refill the reservoir or to maintain the volume of the reservoir. The access port (also referred to herein as an "inlet") is generally sealed and resealable, e.g., via a septum, or iris-type diaphragm, so as to prevent leakage of drug formulation from the reservoir. The access port may be provided in any form, including, but not limited to, a septum, a diaphragm, a cylindrical extension, and the like.

In some embodiments, described in more detail below, a circulating system is provided, which allows exit of formulation substantially depleted of drug from the reservoir. In these embodiments, the first layer further comprises an outlet through which formulation substantially depleted of drug ("spent formulation" or "solvent") can exit, either directly into the peritoneal cavity, or into a tube from which the spent formulation can exit the body. The outlet is a porous, or selectively permeable portion of the first layer (such that drug does not pass through), and thus is adapted for exit of spent formulation without substantial loss of drug remaining in the formulation through the outlet.

The first layer of the patch may comprise a substantially drug-impermeable and liquid-impermeable biocompatible material(s). The first layer may itself comprise more than one layer, e.g., it may be a laminate. Non-limiting examples of first layer materials are polyester, polyurethane, polyether, fabrics impregnated with film rendering the fabrics impervious to the drugs and vehicles, regenerated cellulose (cellophane), ABS polymer/cellulose acetate, ethyl cellulose, copolymers of plasticized vinylacetate vinylchloride, polyethylene terephthlate; polyethylene, polypropylene, nylon film or nylon fabric impregnated with drug impervious films, polyvinylidene chloride, silicone rubber, natural rubber, polyethylene vinyl acetate, impregnated and coated papers and metallic foils, metalized shaped films of PVC, ABS and other shapeable polymeric sheets or films. The first layer may comprise a selectively permeable membrane comprised of a microporous polymer which can be used to exclude transport of compounds having greater than a predetermined molecule weight. Suitable materials include, without limitation, polycarbonates i.e., linear polyesters of carbonic acids in which carbonate groups recur in the polymer chain by phosgenation of a dihydroxy aromatic such as bisphenol A, polyvinylchlorides, polyamides such as polyhexamethylene adipamide and other such polyamides commonly known as "nylon", modacrylic copolymers such as those formed of polyvinylchloride and acrylonitrile, and styrene-acrylic acid copolymers, polysulfones such as those characterized by diphenylene sulfone groups in the linear chain thereof, halogenated polymers such as polyvinylidene fluoride and polyvinylfluoride, polychloroethers and thermoplastic polyethers, acetal polymers such as polyformaldehyde, acrylic resins such as polyacrylonitrile, polymethyl methacrylate and poly n-butyl methacrylate, polyurethanes, polyimides, polybenzimidazoles, polyvinyl acetate, aromatic and aliphatic polyethers, cellulose esters such as cellulose triacetate, cellulose, collodion, epoxy resins, olefins such as polyethylene and polypropylene, porous rubber, cross-linked poly(ethylene oxide), cross-linked polyvinylpyrrolidone, cross-linked poly(vinyl alcohol); derivatives of polystyrene such as poly (sodium styrenesulfonate) and polyvinylbenzyltrimethyl-ammonium chloride, poly(hydroxyethyl methacrylate), poly(isobutyl vinyl ether), polyisoprenes, polyalkenes, ethylene vinyl acetate copolymers such as those described in U.S. Pat. No. 4,144,317, incorporated herein by reference, polyamides, polyurethanes, polyethylene oxides, polyox, polyox blended with polyacrylic acid or Carbopol™, cellulose derivatives such as hydroxypropyl methyl cellulose, hydroxyethyl cellulose, hydroxypropyl cellulose, pectin, starch, guar gum, locust bean gum, and the like, along with blends thereof.

The reservoir portion of the first layer may be impressed or molded into the polymeric and impregnated materials or may be formed by sealing the peripheries of impervious material layers to form a pouch which, together with the outer surface of the organ, or the second layer, forms a drug reservoir. The patch may be manufactured using techniques that are standard in fabrication of transdermal patches, such as casting, extruding, or heat sealing.

Reservoir and Formulation Within the Reservoir

The first layer and the outer surface of the organ together define a drug formulation reservoir. In embodiments which further comprise a second layer, the first and second layers together define a drug formulation reservoir. The drug formulation reservoir may be so formed as to accommodate from about 0.02 ml to at least about 250 ml, from about 0.03 ml to about 100 ml, from about 0.05 ml to about 50 ml, from about 0.1 ml to about 10 ml, from about 0.2 ml to about 5 ml, from about 0.5 ml to about 2.5 ml, or from about 0.75 to about 1.5 ml of drug formulation, or any volume range overlapping or intermediate between the foregoing ranges. The size of the reservoir is determined, in part, by the volume of the unit dose to be administered.

The reservoir may be in any of a variety of shapes, including, but not limited to, square, rectangular, circular, oval or irregular in form. In addition, more than one reservoir may be formed by the first layer and the organ surface, or the first and second layers. The reservoir may be pre-filled with a formulation for delivery prior to placement of the patch in the subject, or may be partially or substantially empty prior to placement, then filled after placement.

Formulation

In some embodiments, the formulation contained within the reservoir includes one or more components that function to limit the rate of diffusion of the drug from the reservoir to the organ. For example, a drug may be provided in a viscous gel (e.g., a biocompatible polyol), or impregnated in a semi-solid polymer matrix. Non-limiting examples of matrices are gels of bipolymers i.e. alginates, gelatins, chitin, polyvinylpyrrolidone (PVP), collagen, polylacticpolyglycolic acid, and polyanhydride. Other non-limiting examples of controlled-release matrices are polyurethane, dimethylpolysiloxane, ethylene vinyl acetate, polymethyl methacrylate, polyamide, polycarbonate, polyester, polyethylene, polypropylene, polyhydroxybutyrate, polystyrene, polyvinyl chloride, polytetrafluoroethylene, and cellulose acetate. Alternatively, the second layer can provide the function of limiting the rate of drug from the reservoir, as discussed in more detail below. In some embodiments, wherein the reservoir is refillable, the rate of delivery to the organ is controlled by the rate of dispensing of drug formulation into the reservoir.

One or more penetration enhancers (also referred to herein as "permeation enhancers" or "absorption enhancers") may be included in the drug formulation. Several chemicals alone or in combination with certain solvents have been noted to promote trans-tissue (e.g., trandermal) penetration. It has been suggested that some of these materials perform their penetration by enlarging the interstitial spaces between the cells of the barrier or enhance solubility of the drug in the barrier. Such penetration vehicles or enhancers are known to the art and many are mentioned in the "Transdermal Delivery of Drugs"; "Drug Permeation Enhancement: Theory and Application" (1994) D. S. Hsieh, ed., Marcel Dekker, Inc., NY; and de Vries et al. (1991) *Crit. Rev. Ther. Drug Carrier Syst.* 8:271–303. Suitable penetration enhancers include, but are not limited to, flux enhancers which may be monovalent, saturated or unsaturated aliphatic, cycloaliphatic or aromatic alcohols having from 4 to 12 carbon atoms, e.g. n-hexanol or cyclohexanol, aliphatic, cycloaliphatic or aromatic hydrocarbons having from 5 to 12 carbon atoms, e.g. hexane, cyclohexane, isopropylbenzene and the like, cyclo-aliphatic or aromatic aldehydes and ketones having from 4 to 10 carbon atoms, such as cyclohexanone, acetamide, N,N-di-lower alkylacetamides such as N,N-dimethylacetamide or N,N-diethylacetamide, C10-C20-alkanoylamides, e.g. N,N-dimethyllauroylamide, methylated beta-cyclodextrin, sodium glycodeoxycholate, N-trimethyl chitosan chloride, taurocholate, glycocholate, sodium cap rate, sodium taurodihydrofusidate, 1-n-C10-C20-alkylazacycloheptan-2-one, e.g. 1-n-dodeclazacycloheptan-2-one(Azone™ laurocapram), or N-2-hydroxyethylacetamide, and known vehicles and/or penetration enhancers such as aliphatic, cycloaliphatic and aromatic esters N,N-di-lower alkylsulphoxides, unsaturated oils, halogenated or nitrated aliphatic or cyclo-aliphatic hydrocarbons, salicylates, polyalkylene glycol silicates, and mixtures thereof. Further suitable permeation enhancers include agents for epithelial transport, including, but not limited to, dimethylsulfoxide, salicylates, surfactants, chelating agents, fatty acids, acid salts, and bile salts.

In other embodiments, the formulation includes one or more components that function to increase the rate of diffusion of the drug from the reservoir to the organ. Inclusion of a water-swellable polymer in the reservoir may increase the rate of drug release per unit time, and in thus the total quantity of drug released. Examples of water-swellable polymers which may be included are products such as galactomannans, cellulose products, tragacanth, polyglycosides, polyvinylpyrrolidones, finely powdered polyamides, water-soluble polyacrylamide, carboxyvinyl polymerisates, agar-like algae products, mixed polymerisates of methyl vinyl ether and maleic acid anhydride, guar rubber, types such as hydroxyphenyl-guar rubber or guar powder, gum arabic, dextrin and dextran, microbiologically produced polysaccharide rubber such as polysaccharide B-1459 or the highly water-soluble type Keltrol or synthetically produced polysaccharides such as the product Ficoll, methyl glucose derivatives, hydroxymethylpropyl cellulose, polycalacturonic acide derivatives such as pectin or the amidated product Pectinamid. Galactomannans, microcrystalline cellulose and tragacanth may also be used. Galactomannans, microcrystalline cellulose, and tragacanth are also suitable.

Exemplary drugs that can be delivered from the reservoir are described in more detail below.

Second Layer

In some embodiments, the patch comprises a second layer. In these embodiment, the second layer comprises an inner drug delivery surface which may be in direct contact with the outer surface of the organ and which is permeable to the drug to be delivered. The second layer may consist entirely of a drug-permeable material, or alternatively, only a portion of the second layer may be drug permeable, with the remaining portion of the second layer comprising a non-permeable material (e.g., materials suitable for the first layer). The drug-permeable portion may comprise a diffusion rate-controlling membrane, which can control, or regulate, the rate of delivery of the drug out of the reservoir and into the organ tissue. The second layer may further comprise an element for affixing the patch to the organ, e.g., an adhesive portion. Alternatively, an affixing element may be provided as a separate element attached to the second layer (see below).

The first and second layers may be separate from one another before being attached to each other during manufacture of the patch. Alternatively, the first and second layers may be continuous with one another, e.g., as shown in FIG. 2.

In some embodiments, the patch comprises a first layer, a second layer, and an attachment element, which are configured and positioned such that the patch envelops substantially all or a portion of the organ outer surface, e.g., the first and second layers can form a sack that substantially surrounds the organ. In one example of this embodiment, the attachment element is generally annular, and forms a seal such that a reservoir is formed between the first and second layers. All or a portion or portions of the second layer can consist of a drug-permeable material.

Drug-permeable Portion

The drug-permeable portion of the second layer, or the entire second layer, may comprise a variety of materials, providing they are biocompatible. The rate of release of the drug from the drug-permeable portion is controlled by a number of factors, including: (1) the porosity of the material (the size and density of the pores); (2) the area of the drug-permeable portion; (3) the thickness of the drug-permeable portion; (4) the diffusion coefficient of the drug, which in turn depends upon the viscosity of the solution in the reservoir; (5) the particle size of the drug; (6) the concentration of the drug in the reservoir relative to the concentration of the drug outside the reservoir; and (7) the solubility of the drug in the drug-permeable membrane.

The rate of release of the drug is controlled to some degree by the porosity of the drug-permeable portion. The size of the pores may be varied, depending on the size of the drug being delivered, and the desired delivery rate. Pore sizes may range from about 5 nm to about 0.1 mm. In addition, the density of the pores may be varied, depending on the desired delivery rate. Pore density may range from about 10 pores/cm$^2$ to about $10^{12}$ pores/cm$^2$, from about $10^2$ pores/cm$^2$ to about $10^{10}$ pores/cm$^2$, from about $10^3$ pores/cm$^2$ to about $10^8$ pores/cm$^2$, or from about $10^4$ pores/cm$^2$ to about $10^6$ pores/cm$^2$, or any intermediate range with these ranges, or any overlapping range within these ranges. The porosity (i.e., the ratio of area containing pores to the total drug-permeable membrane area) will range from about 0 to about 95%.

The drug-permeable portion of the second layer can be microporous or dense without pores. Dense membranes can transport drug molecules by a solution diffusion mechanism, which is well described in the literature. See, e.g., "Controlled Release of Biologically Active Agents," (1987) R. Baker, John Wiley & Sons.

The area of the drug-permeable portion is generally in the range of about 0.5 cm$^2$ to about 20 cm$^2$, from about 1 cm$^2$ to about 10 cm$^2$, or from about 2 cm$^2$ to about 5 cm$^2$. The drug-permeable portion may be in any shape, such as circular, square, rectangular, or may be irregular in shape.

The second layer may comprise more than one drug-permeable portions, which may be arranged in any manner (e.g., in rows, or in a random arrangement).

The drug-permeable portion of the second layer may comprise an organic or synthetic polymer, including, but not limited to, polypropylene, polytetrafluoroethylene, polycarbonates, polyvinylchloride, cellulose acetate, cellulose nitrate, and polyacrylonitrile. Other suitable materials include, without limitation, polycarbonates i.e., linear polyesters of carbonic acids in which carbonate groups recur in the polymer chain by phosgenation of a dihydroxy aromatic such as bisphenol A, polyvinylchlorides, polyamides such as polyhexamethylene adipamide and other such polyamides commonly known as "nylon", modacrylic copolymers such as those formed of polyvinylchloride and acrylonitrile, and styrene-acrylic acid copolymers, polysulfones such as those characterized by diphenylene sulfone groups in the linear chain thereof, halogenated polymers such as polyvinylidene fluoride and polyvinylfluoride, polychloroethers and thermoplastic polyethers, acetal polymers such as polyformaldehyde, acrylic resins such as polyacrylonitrile, polymethyl methacrylate and poly n-butyl methacrylate, polyurethanes, polyimides, polybenzimidazoles, polyvinyl acetate, aromatic and aliphatic polyethers, cellulose esters such as cellulose triacetate, cellulose, collodion, epoxy resins, olefins such as polyethylene and polypropylene, porous rubber, cross-linked poly(ethylene oxide), cross-linked polyvinylpyrrolidone, cross-linked poly(vinyl alcohol); derivatives of polystyrene such as poly (sodium styrenesulfonate) and polyvinylbenzyltrimethyl-ammonium chloride, poly(hydroxyethyl methacrylate), poly(isobutyl vinyl ether), polyisoprenes, polyalkenes, ethylene vinyl acetate copolymers such as those described in U.S. Pat. No. 4,144,317, incorporated herein by reference, polyamides, polyurethanes, polyethylene oxides, polyox, polyox blended with polyacrylic acid or Carbopol™, cellulose derivatives such as hydroxypropyl methyl cellulose, hydroxyethyl cellulose, hydroxypropyl cellulose, pectin, starch, guar gum, locust bean gum, and the like, along with blends thereof.

In some embodiments, the second layer is bioerodable. In these embodiments, drug is released during the erosion process.

Element for Affixing the Patch to an Organ Surface

An element for affixing the patch to an organ is generally a tissue adhesive. Thus, the element for affixing the patch to an area of the organ may be an adhesive portion(s) of the first layer, or, if present, the second layer. Alternatively, the element for affixing the patch to an area of the organ may be a separate element attached to the first layer or the second layer.

The adhesive portion may be in any of a variety of configurations, as long as the patch is affixed to the organ surface. The adhesive portion may completely or partially surround the edge of the drug delivery patch (e.g., surround the first layer or the second layer, or the drug-permeable portion of the second layer). The adhesive portion may comprise tissue adhesive in a single or multiple discreet areas or spots, or may be configured in a continuous manner, such as a ring, a rectangle, or some variation thereof.

Tissue adhesives are known in the art, and any of these may be used to secure a patch of the invention to the organ surface. Tissue adhesives have been amply described in the literature. See, e.g. U.S. Pat. Nos. 6,034,140; 5,985,312; 5,292,362; and 5,290,552, the contents of which are incorporated herein by reference for their teachings regarding tissue adhesives. Also of interest is the use of BioGlue® which is commercially available (CryoLife, Inc.). Other suitable adhesives include fibrin-, fibrinogen-, and thrombin-based sealants, bioactive ceramic-based sealants, and cyanoacrylate sealants, including, but not limited to, Vitex (V.I. Technologies, NY; comprising thrombin:fibrinogen in a 1:1 ratio); Quixil (Omrix Biopharm SA, Brussels); Dermabond, an octylcyanoacrylate tissue adhesive (Bruns and Worthington (2000) *Am. Fam. Physician* 61:1383–1388); Tisseel (Baxter International, Deerfield, Ill.); Hemaseel APR (Haemacure, Sarasota, Fla.); PlasmaSeal (Plasmaseal, San Francisco, Calif.); AutoSeal (Harvest Technologies, Norwell, Mass.); Floseal (Fusion Medical Technologies, Mountain View, Calif.); and Bioglass (U.S. Biomaterials, Alachua, Fla.); CoStasis (Cohesion Technologies). *MedPro Month* (*1999*) 9:261–262; and *MedPro Month* (2000) 10:86–91.

A bioresorbable adhesive may be formed by forming intermacromolecular complexes of a carboxypolysaccharide and, optionally, a polyether, such as polyethylene oxide. The carboxypolysaccharide may be of any biocompatible sort, including but not limited to carboxymethyl cellulose (CMC), carboxyethyl cellulose, chitin, hyaluronic acid, starch, glycogen, alginate, pectin, carboxymethyl dextran, carboxymethyl chitosan, and glycosaminoglycans such as heparin, heparin sulfate, and chondroitin sulfate.

In some embodiments, the patch is manufactured with an adhesive element that is ready for attachment to an organ, i.e., the adhesive will adhere to the organ surface upon contact (e.g., the adhesive element is a moist tissue adhesive). In some of these embodiments, the attachment element(s) may be covered by a release liner, as described further below. Alternatively, the patch may be-manufactured dry, and, upon contact with the organ surface, it can hydrate and self-adhere to the organ surface.

The patch of the invention can also be affixed to the organ surface by means of sutures, hooks, needles and other mechanical fasteners known to those skilled in the art. Such exemplary attachment elements again can be part of the first layer for the second layer or can be a separate element.

Additional Components

The implantable patch may further comprise a release liner, e.g., a strippable, protective coating that covers at least the drug-permeable and adhesive portions of the drug delivery patch. Just prior to use, the coating is peeled away from the patch, exposing either the drug reservoir or the second layer, and discarded. The coating may comprise the same materials as the first layer, with the provision that the coating is made strippable, e.g., by siliconizing. Where the patch comprises a release liner, the release liner may provide for a temporary reservoir between the first layer and the release liner, which reservoir can be pre-filled with a drug formulation (preferably with a gelled or other slow-flowing formulation comprising drug).

Patch With Refillable Reservoir

In some embodiments, the drug reservoir is refillable. Refilling the reservoir may be accomplished in various ways. For example, the first layer may comprise an access port or a septum plug, comprising a resealable material, which permits a needle of a syringe containing drug to be inserted and drug injected into the reservoir from the syringe. Alternatively, a distal end of a catheter is connected, directly or indirectly, to the drug reservoir. The portion of the first layer which is directly over the reservoir may comprise an element for connecting the catheter. A connection element may be integral to the first layer, or may be a separate element stably positioned in the patch first layer, or, in some embodiments, may be removably positioned in the patch first layer. For example, a connection element may be a short tube which penetrates the first layer, forming a conduit from outside the patch to the reservoir. A first (proximal) end of the tube may be closed, e.g., by a septum which can be accessed via a needle on the distal end of the catheter. A second (distal) end of the tube enters the reservoir.

A catheter may be stably attached to the implantable patch via a connection element. Accordingly, in some embodiments, an implantable patch of the invention is provided with a catheter stably attached to the first layer. For example, the catheter and patch can be pre-assembled. In these embodiments, a delivery device can be attached, permanently or removably, to the catheter proximal end.

The proximal end of the catheter may be attached to a drug delivery device, from which the drug is delivered, flows through the catheter, and into the drug reservoir of the patch. The catheter distal end may be attached to the connection element proximal end. Alternatively, the catheter distal end may be inserted completely or partially through the connection element.

In some embodiments, the reservoir is configured to allow a drug solution to circulate or flow from a drug delivery device past the drug permeable portion of the second layer, e.g., a "continuous flow-through" system. In this embodiment, the first layer has an inlet through which drug enters from the delivery device, and an outlet, from which solvent substantially depleted of drug exits the reservoir. As described above, the area of the first layer which forms the outlet comprises a membrane which allows exit of solvent, but which does not allow exit of drug from the reservoir. A continuous flow-through system allows maintenance of a concentration gradient across the drug-permeable portion of the second layer or across the organ surface.

Drugs Suitable for Delivery Via an Implantable Patch of the Invention

Any of a variety of drugs can be delivered according the methods of the present invention. The drug delivered will vary according to the target organ to which the patch is to be affixed, and the condition to be treated. Drugs provided herein are exemplary, and are not meant to be limiting in any way.

Antiinflammatory agents include, but are not limited to, any known non-steroidal antiinflammatory agent, and any known steroidal antiinflammatory agent. Antiinflammatory agents include, but are not limited to, any known nonsteroidal antiinflammatory agent such as, salicylic acid derivatives (aspirin), para-aminophenol derivatives (acetaminophen), indole and indene acetic acids (indomethacin), heteroaryl acetic acids (ketorolac), arylpropionic acids (ibuprofen), anthranilic acids (mefenamic acid), enolic acids (oxicams) and alkanones (nabumetone) and any known steroidal antiinflammatory agent which include corticosteriods and biologically active synthetic analogs with respect to their relative glucocorticoid (metabolic) and mineralocorticoid (electrolyte-regulating) activities. Additionally, other drugs used in the therapy of inflammation or antiinflammatory agents including, but are not limited to, the autocoid antagonists such as all histamine and bradykinin receptor antagonists, leukotriene and prostaglandin receptor antagonists, and platelet activating factor receptor antagonists.

Antimicrobial agents include antibiotics (e.g. antibacterial), antiviral agents, antifungal agents, and antiprotozoan agents. Non-limiting examples of antimicrobial agents are sulfonamides, trimethoprim-sulfamethoxazole, quinolones, penicillins, and cephalosporins.

Antineoplastic agents include, but are not limited to, those which are suitable for treating tumors that may be present on or within an organ (e.g., myxoma, lipoma, papillary fibroelastoma, rhabdomyoma, fibroma, hemangioma, teratoma, mesothelioma of the AV node, sarcomas, lymphoma, and tumors that metastasize to the target organ) including cancer chemotherapeutic agents, a variety of which are well known in the art.

Angiogenic factors (e.g., to promote organ repair or for development of a biobypass to avoid a thrombosis) include, but are not limited to, basic fibroblast growth factor, acidic fibroblast growth factor, vascular endothelial growth factor, angiogenin, transforming growth factor $\alpha$ and $\beta$, tumor necrosis factor, angiopoietin, platelet-derived growth factor, placental growth factor, hepatocyte growth factor, and proliferin.

Thrombolytic agents include, but are not limited to, urokinase plasminogen activator, urokinase, streptokinase, inhibitors of $\alpha 2$-plasmin inhibitor, and inhibitors of plasminogen activator inhibitor-1, angiotensin converting enzyme (ACE) inhibitors, spironolactone, tissue plasminogen activator (tPA), an inhibitor of interleukin $1\beta$ converting enzyme, anti-thrombin III, and the like.

Where the target organ is the heart, exemplary drugs for delivery include, but are not necessarily limited to, growth factors, angiogenic agents, calcium channel blockers, antihypertensive agents, inotropic agents, antiatherogenic agents, anti-coagulants, $\beta$-blockers, anti-arrhythmia agents, cardiac glycosides, antiinflammatory agents, antibiotics, antiviral agents, antifungal agents, agents that inhibit protozoan infections, and antineoplastic agents.

Calcium channel blockers include, but are not limited to, dihydropyridines such as nifedipine, nicardipine, nimodipine, and the like; benzothiazepines such as diltazem; phenylalkylamines such as verapamil; diarylaminopropylamine ethers such as bepridil; and benzimidole-substituted tetralines such as mibefradil.

Antihypertensive agents include, but are not limited to, diuretics, including thiazides such as hydroclorothiazide, furosemide, spironolactone, triamterene, and amiloride; antiadrenergic agents, including clonidine, guanabenz, guanfacine, methyldopa, trimethaphan, reserpine, guanethidine, guanadrel, phentolamine, phenoxybenzamine, prazosin, terazosin, doxazosin, propanolol, methoprolol, nadolol, atenolol, timolol, betaxolol, carteolol, pindolol, acebutolol, labetalol; vasodilators, including hydralizine, minoxidil, diazoxide, nitroprusside; and angiotensin converting enzyme inhibitors, including captopril, benazepril, enalapril, enalaprilat, fosinopril, lisinopril, quinapril, ramipril; angiotensin receptor antagonists, such as losartan; and calcium channel antagonists, including nifedine, amlodipine, felodipine XL, isadipine, nicardipine, benzothiazepines (e.g., diltiazem), and phenylalkylamines (e.g. verapamil).

Anti-coagulants include, but are not limited to, heparin; warfarin; hirudin; tick anti-coagulant peptide; low molecular weight heparins such as enoxaparin, dalteparin, and arde-parin; ticlopidine; danaparoid; argatroban; abciximab; and tirofiban.

Antiarrhythmic agents include, but are not necessarily limited to, sodium channel blockers (e.g., lidocaine, procainamide, encainide, flecanide, and the like), beta adrenergic blockers (e.g., propranolol), prolongers of the action potentila duration (e.g., amiodarone), and calcium channel blockers (e.g., verpamil, diltiazem, nickel choride, and the like). Delivery of cardiac depresssants (e.g., lidocaine), cardiac stimulants (e.g., isoproterenol, dopamine, norepinephrine, etc.), and combinations of multiple cardiac agents (e.g., digoxin/quinidine to treat atrial fibrillation) is also of interest.

Agents to treat congestive heart failure, include, but are not limited to, a cardiac glycoside, inotropic agents, a loop diuretic, a thiazide diuretic, a potassium ion sparing diuretic, an angiotensin converting enzyme inhibitor, an angiotensin receptor antagonist, a nitrovasodilator, a phosphodiesterase inhibitor, a direct vasodilator, an $\alpha_1$-adrenergic receptor antagonist, a calcium channel blocker, and a sympathomimetic agent.

Agents suitable for treating cardiomyopathies include, but are not limited to, dopamine, epinephrine, norepinephrine, and phenylephrine.

Also suitable are agents that prevent or reduce the incidence of restenosis; including, but not limited to, taxol (paclataxane) and related compounds; and antimitotic agents.

Drug Delivery Systems of the Invention

The invention further provides a drug delivery system for delivery of a therapeutic agent to an organ, comprising an implantable patch of the invention; and a catheter having proximal and distal ends, the distal end of the catheter being operably attached to the patch; and a drug delivery device operably attached to the proximal end of the catheter. The drug delivery device may be one that provides for low volume rate delivery of drug formulation to the patch. The drug delivery device may be one that provides for circulation of the drug formulation through the patch.

Drug Delivery Devices

Drug delivery devices suitable for use with the patch of the present invention can take advantage of any of a variety of controlled drug release devices. In general, the drug release devices suitable for use in the invention comprise a drug reservoir for retaining a drug formulation or alternatively some substrate or matrix which can hold drug (e.g., polymer, binding solid, etc.). The drug release device can be selected from any of a variety of controlled drug delivery system known in the art. In some embodiments, the drug delivery system is implantable. Controlled drug release devices suitable for use in the present invention generally can provide for delivery of the drug from the device at a selected or otherwise patterned amount and/or rate to the drug delivery patch.

Release of drug from the drug delivery device, particularly controlled release of drug to the patch, can be accomplished in any of a variety of ways according to methods well known in the art, e.g., by incorporation of drug into a polymer that provides for substantially controlled diffusion of drug from within the polymer, incorporation of drug in a biodegradable polymer, providing for delivery of drug from an osmotically-driven device, etc. Where the drug delivery device comprises a drug delivery catheter, drug can be delivered through the drug delivery catheter to the patch as a result of capillary action, as a result of pressure generated from the drug release device, by diffusion, by electrodiffusion or by electroosmosis through the device and/or the catheter.

Drug release devices suitable for use in the invention may be based on any of a variety of modes of operation. For example, the drug release device can be based upon a diffusive system, a convective system, or an erodible system (e.g., an erosion-based system). For example, the drug release device can be an osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, etc.

Drug release devices based upon a mechanical or electromechanical infusion pump, can also be suitable for use with the present invention. Examples of such devices include those described in, for example, U.S. Pat. Nos. 4,692,147; 4,360,019; 4,487,603; 4,360,019; 4,725,852, and the like. In general, the present methods of drug delivery can be accomplished using any of a variety of refillable, non-exchangeable pump systems. Pumps and other convective systems are generally preferred due to their generally more consistent, controlled release over time. Osmotic pumps are particularly preferred due to their combined advantages of more consistent controlled release and relatively small size. Of the osmotic pumps, the DUROS™ osmotic pump is particularly preferred (see, e.g., WO 97/27840 and U.S. Pat. Nos. 5,985,305 and 5,728,396)).

In one embodiment, the drug release device is a controlled drug release device in the form of an osmotically-driven device. Preferred osmotically-driven drug release systems are those that can provide for release of drug in a range of rates, which rates will vary with the drug potency and the concentration fo drug in the formulation. Exemplary drug delivery rates range from about 0.01 $\mu$g/hr to about 200 $\mu$g/hr (which formulation can be delivered at a volume rate of from about 0.01 $\mu$l/day to about 100 $\mu$l/day (i.e., from about 0.0004 $\mu$l/hr to about 4 $\mu$l/hr), preferably from about 0.04 $\mu$l/day to about 10 $\mu$l/day, generally from about 0.2 $\mu$l/day to about 5 $\mu$l/day, typically from about 0.5 $\mu$l/day to about 1 $\mu$l/day). In one embodiment, the volume/time delivery rate is substantially constant (e.g., delivery is generally at a rate ± about 5% to 10% of the cited volume over the cited time period.

In some embodiments, drug delivery devices of interest for use in conjunction with a drug delivery patch of the invention are those that can deliver drug at a low volume rate e.g., on the order of nanoliters to microliters per day. In one embodiment, a volume rate of from about 0.01 $\mu$l/day to about 2 ml/day is accomplished by delivery of about 80 $\mu$l/hour over a period of 24 hours, with the delivery rate over that 24 hours period fluctuating over that period by about ±5% to 10%. Exemplary osmotically-driven devices suitable for use in the invention include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like.

Flow-through System Comprising Patch and Drug Delivery Device

In some embodiments, the drug delivery device and the implantable patch are configured to allow a drug solution to circulate or flow through the drug reservoir, e.g., a "continuous flow-through system" (also referred to herein as a "circulating system."). A circulating system allows maintenance of the drug concentration in the reservoir at a relatively constant level, e.g., the concentration of drug in the reservoir varies by no more than about ±25%, about ±10%, about ±5%, or about ±2%, from the starting concentration. By maintaining drug concentration in the reservoir at a relatively constant level, the concentration gradient across the organ surface can be maintained at a relatively constant level. In these embodiments, the first layer has an inlet through which drug enters from the delivery device, and an outlet, from which solvent substantially depleted of drug ("spent formulation" or "solvent") exits the reservoir.

In the circulating system embodiment, the drug delivery system may comprise a catheter through which drug formulation flows into the reservoir through an inlet in the first layer. Movement of solvent out of the reservoir can be accomplished by providing an element in the first layer that allows for release of solvent, generally selective release of solvent from the reservoir, e.g., allows for release of spent formulation without substantial or significant release of drug in the reservoir. The solvent release element can be, for example, an outlet tube from which formulation substantially depleted of drug exits the reservoir through the outlet in the first layer. The outlet tube can provide for selective release of solvent (e.g., by incorporating a selective membrane or a microporous membrane, as described below). Alternatively, the solvent release element can be a selective membrane positioned at one or more sites on the first layer, and can be comprise the material of all or a portion of the first layer. The solvent substantially depleted of drug can exit the release element into the body (e.g., into the peritoneal cavity). Alternatively, solvent substantially depleted of drug can be collected into a collection pouch. As a further alternative, solvent substantially depleted of drug can be directed out of the body. This can be accomplished by having the outlet tube exit the body, generally through the same entry point as the catheter.

Methods of Drug Delivery Using an Implantable Patch of the Invention

The present invention provides methods of treating an individual by administering a therapeutically active drug via a drug delivery system according to the invention.

In operation, a patch of the invention is attached to the outer surface of an organ by the affixing element. The patch of the invention can be placed on the organ for drug delivery in the course of surgery, e.g., to delivery drugs to facilitate recovery of the subject from surgery, to avoid post-operative complications (e.g., post-operative arrhythmia where the target organ is the heart and the like). The patch can also be placed on an organ outer surface of the using minimally invasive techniques well known to those skilled in the art, including, but not limited to, laparoscopic techniques.

The delivery device of the invention can be used alone or as an adjunct to other therapeutic regimen (e.g. oral or intravenous therapy, etc.). The device can be used in connection with procedures such as catheterization, routine surgeries, and in the case of the heart, coronary arteriography, angioplasty, and clinical electrophysiology studies. For example, the patch of the invention can be placed on the heart in the course of implantation of a pacemaker or other therapeutic device.

Suitable Target Organs and Subjects

The implantable patch of the invention can be adapted for and/or sized for use to deliver drug to any desired internal organ. Of particular interest is delivery to an organ that retains or accumulates drug at the treatment site (e.g., at, surrounding, within, or on the organ), so as to provide a local advantage concomitant with site-specific delivery to the organ. In other embodiments, the drug delivery to the organ can be associated with delivery into the circulatory system to provide for systemic delivery of a drug (e.g., by delivery to an artery of the heart). The organ need not be intact in its anatomical structure. Exemplary organs and other defined anatomical structures to which drug can be delivered using an implantable patch of the invention include, but are not necessarily limited to heart, liver, kidney, pancreas, prostate, ovary, uterus, brain, stomach, intestine, lung, lymph nodes, joint capsules, and the like.

Subjects suitable for treatment according to the methods of the present invention include individuals suffering from a condition, such as, but not limited to, a microbial infection of an organ; inflammation; thrombosis; and, an ischemic disease of the target organ. Where the heart is the organ, additional conditions suitable for treatment include, but are not limited to, arrhythmia; a cardiomyopathy; coronary angioplasty restenosis; myocardial infarction; cardiac tamponade; pericardial effusion; atherosclerosis; a cardiac condition related to hypertension; congestive heart failure; and a cardiac neoplasm.

In addition, subjects at risk for developing such conditions are suitable for treatment using the methods of the present invention. For example, subjects who are at risk for developing a cardiac condition include individuals who have undergone coronary angioplasty; individuals with a history of a cardiac condition; individuals predisposed to developing a cardiac condition, as a result of a genetic predisposition, as a result of a metabolic disorder, or as a result of diet, behavior, as a result of another disease (e.g., diabetes, HIV infection), and the like; individuals who are in remission for a cardiac neoplasm; and hypertensive individuals.

Atherosclerosis and conditions that predipose to pathological atherosclerotic plaques (e.g., in the coronary arteries) include, but are not limited to, lipid/cholesterol deposition; macrophage/inflammatory cell recruitment; plaque rupture; thrombosis; platelet deposition; and neointimal proliferation.

Where the target organ is the heart, ischemic disease and attendant syndromes include, but are not limited to, myocardial infarction; stable and unstable angina; coronary artery restenosis following percutaneous transluminal coronary angioplasty; and reperfusion injury.

Myopathies of a target include, but are not limited to, myopathies caused by or associated with ischemic syndromes; toxins such as alcohol, and chemotherapeutic agents such as adriamycin; microbial infections of organ tissue or associated fluids, (or deleterious effects of microbial infections of other tissues (e.g., toxin production)), due to any microbial agent to including viruses, e.g. cytomegalovirus, human immuodeficiency virus, echovirus, influenza virus, adenovirus; bacteria, including, but not limited to, *Mycobacterium tuberculosis*, meningococci, spirochetes, viridans Streptococci, (e.g., *S. sanguis, S. oralis, S. salivarus. S. mutans*), Enterococci, Staphylococci (e.g., *S. aureus, S. epidermidis*), *Haemophilus parainfluenzae, Haemophilus aphrophilus, Eikenella corrdens, Kingella kingae, Actinobacillus actinomycetemcomitans, Cardiobacterium hominus*; protozoans, such as *Trypanosoma cruzi*; and fungi, including, but not limited to, *Candida parapsilosis, Candida albicans*, and *Candida tropicalis*; hypertension; metabolic disorders, including, but not limited to, uremia, and glycogen storage disease; radiation; neuromuscular disease (e.g., Duchennes' muscular dystrophy); infiltrative diseases (e.g., sarcoidosis, hemochromatosis, amyloidosis); trauma; and idiopathic causes.

Inflammatory conditions of organs include, but are not limited to, immune rejection, and conditions resulting from idiopathic, autoimmune, or connective tissue diseases. Where the organ is the heart, exemplary inflammatory conditions include myocarditis, pericarditis, and endocarditis.

Microbial infections of organ tissues may be bacterial, viral, fungal, or parasitic (e.g., protozoan) in origin (see above for non-limiting list of microbial infectious agents).

Exemplary Embodiments of the Invention

Exemplary, non-limiting embodiments of the invention will now be described with reference to the figures.

Figure 1A:
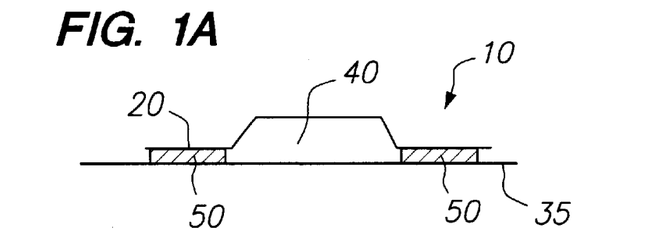
FIG. 1 depicts an exemplary embodiment of an implantable patch of the invention.
Figure 1B:
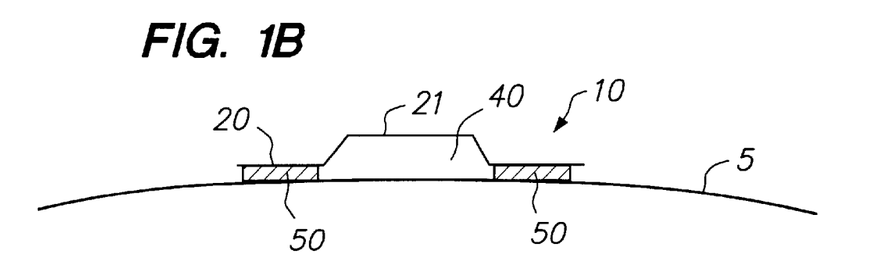

FIGS. 1A and 1B depict a non-limiting embodiment of the invention. FIG. 1A shows a cut-away view of an exemplary patch 10 comprising a first layer 20 and an adhesive or attachment element 50 for attaching the first layer to an outer surface of an organ. Attachment element may be integral with the first layer, or may be a separate element which is affixed to the first layer. Optionally, a release liner 35 overlays the adhesive portion of the first layer, and is removed before placement of the first layer on an organ surface. FIG. 1B shows the patch 10 of FIG. 1A, from which the release liner has been removed. Patch 10 is placed in contact with an outer surface 5 of an organ. Together, the reservoir portion 21 of the first layer 20 and the organ surface 5 form a reservoir 40.

Figure 2A:
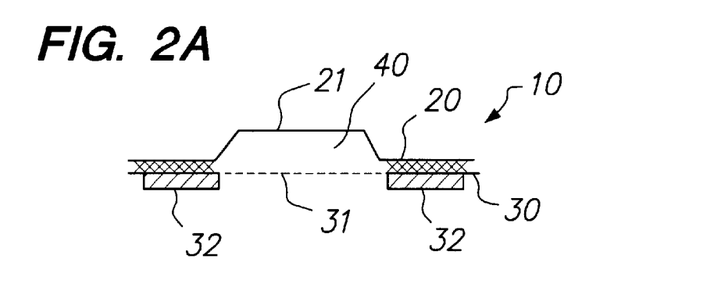
FIGS. 2A–D depict exemplary embodiments of an implantable delivery patch of the invention.
Figure 2B:
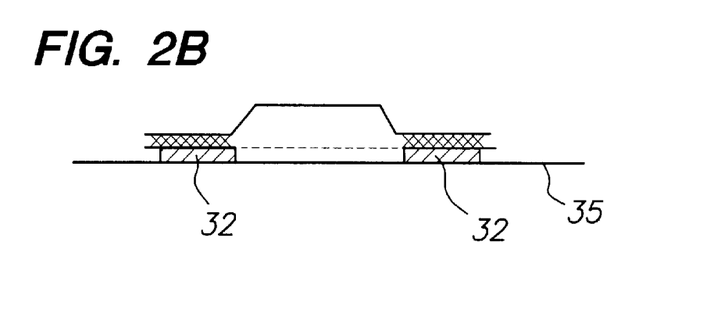

FIGS. 2A–D depict various non-limiting embodiments of the invention. FIG. 2A shows a cut-away view of an exemplary patch 10 comprising a first layer 20 and a second layer 30. First and second layers together form a drug reservoir 40. First and second layers are attached to one another (as indicated by cross-hatching) except at the portions forming the reservoir. First layer 20 has been impressed to form a raised portion 21 which forms the upper, organ surface-distal, side of reservoir 40. Second layer 30 comprises a drug-permeable portion 31, which forms the lower, organ surface-proximal, side of the reservoir. Second layer 30 further comprises one or more attachment elements, which may be separate elements or, as shown here, may be adhesive portions 32 of the second layer which serve to affix the patch to the organ surface. FIG. 2B shows a cut-away view of a patch which further comprises a release liner 35. Release liner 35 covers the adhesive portion 32 until just prior to use, when the release liner is removed and discarded.

Figure 2C:
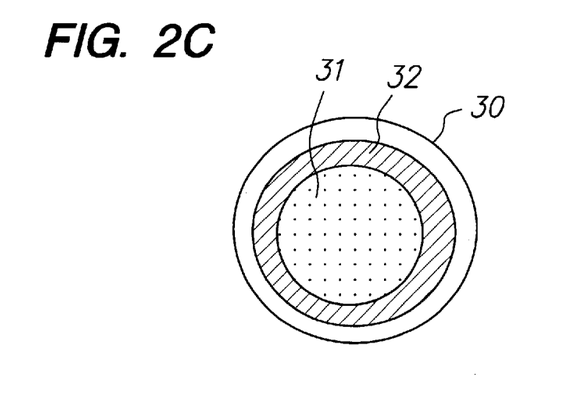
Figure 2D:
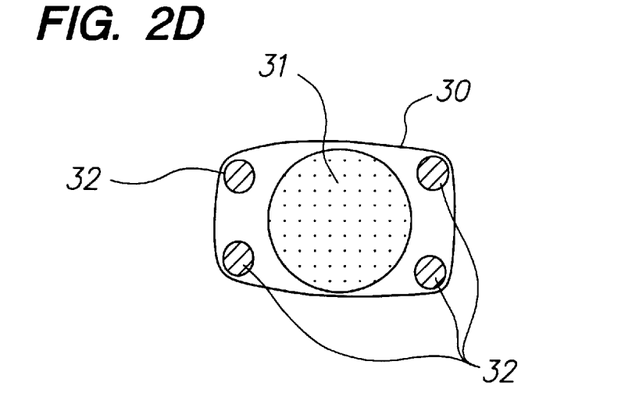

FIGS. 2C and 2D depict views of exemplary patches viewed from the second layer side. FIG. 2C shows the adhesive portion 32 of the second layer 30 surrounding the drug-permeable portion 31. FIG. 2D shows an embodiment in which several adhesive spots 32 are arranged around the drug-permeable portion 31.

Figure 3:
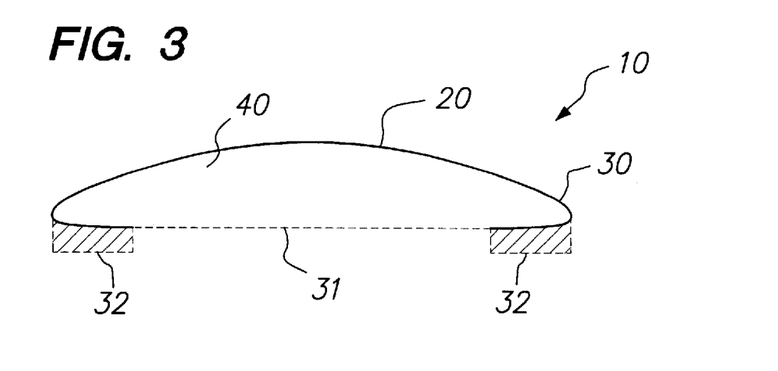
FIG. 3 depicts a further exemplary embodiment of an implantable delivery patch of the invention in which the first and second layers are continuous.

FIG. 3 depicts another exemplary embodiment of an implantable drug-delivery patch of the invention. In this embodiment, first layer 20 and second layer 30 are continuous with one another.

Figure 4A:
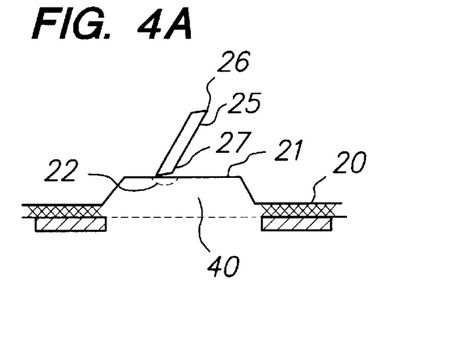
FIG. 4 depicts an exemplary embodiment of a refillable implantable delivery patch of the invention.
Figure 4B:
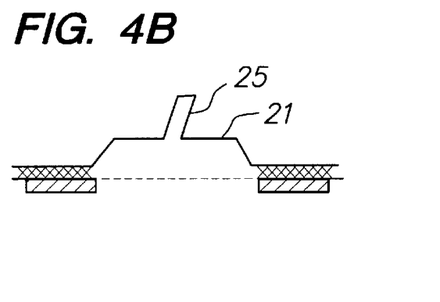
Figure 4C:
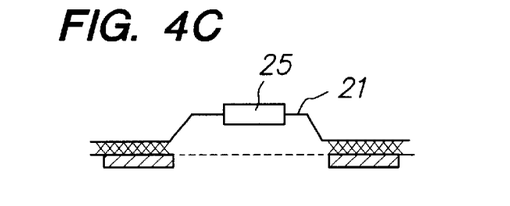

FIGS. 4A–4C depict further exemplary embodiments of a drug-delivery patch comprising a refillable reservoir. In the embodiment shown in FIG. 4A, reservoir portion 21 of first layer 20 comprises an inlet 22 through which drug formulation flows, either directly from a catheter (not shown), or via a connection element 25. In this embodiment, an connection element 25 is shown, the connection element having a first end 26 and a second end 27. The connection element first end 26 is adapted for connection to a catheter (not shown). The connection element second end 27 provides an entry point for drug formulation delivered to the reservoir 40 via a catheter. This embodiment is particularly suited for use with low volume rate drug delivery devices. FIG. 4B shows an embodiment in which connection element 25 is integral with reservoir portion 21 of first layer 20. FIG. 4C shows a further embodiment in which connection element is a septum or access port.

Figure 5A:
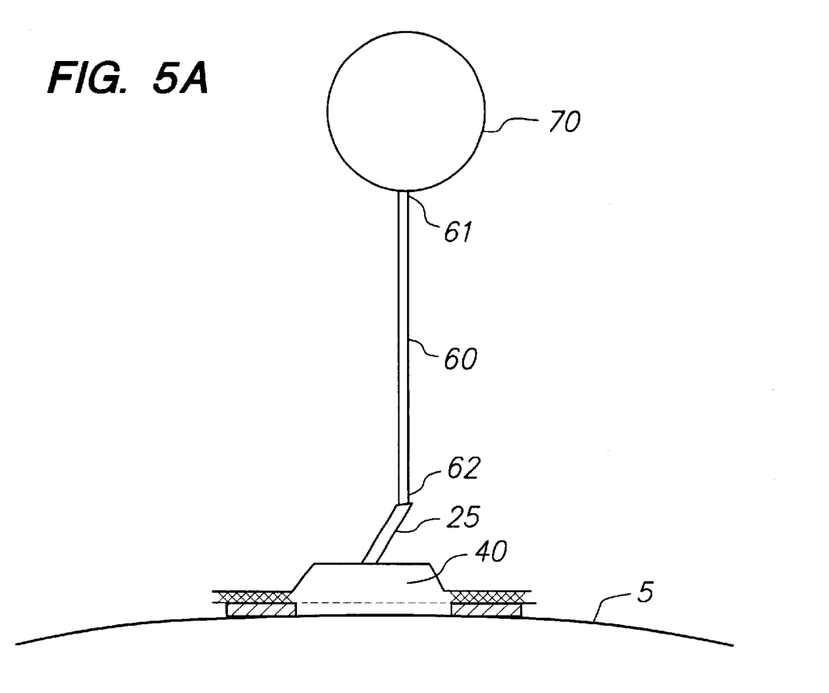
FIGS. 5A and 5B depict different views of an exemplary embodiment of a drug delivery system of the invention.
Figure 5B:
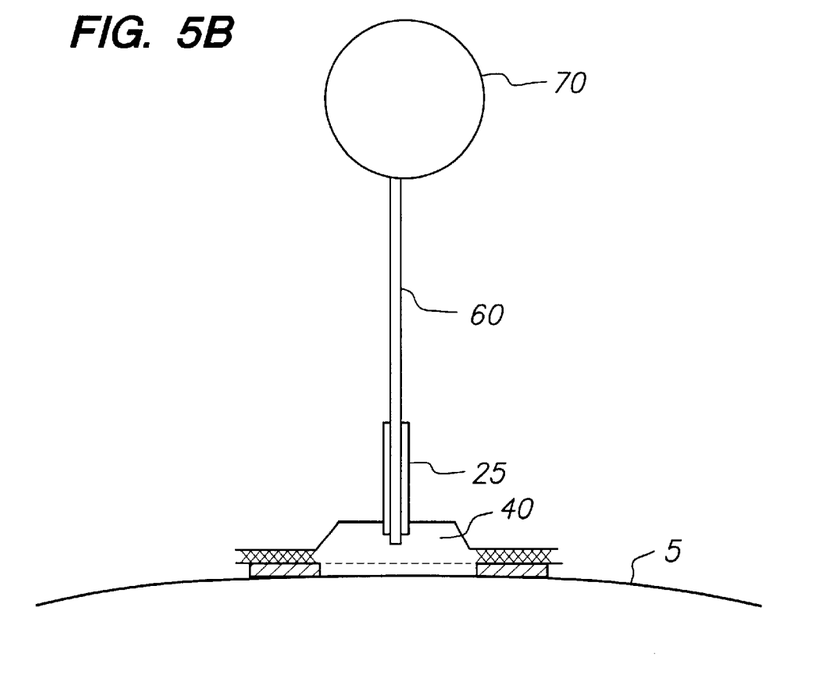

FIGS. 5A and 5B depict different views of an exemplary drug delivery system of the invention. In FIG. 5A, drug-delivery patch 10 is affixed to organ surface 5. Catheter 60 comprises proximal 61 and distal 62 ends. Catheter proximal end 61 is attached to a drug delivery device 70. Catheter distal end 62 is attached, generally via an attachment element 25 which provides entry into the drug reservoir 40. FIG. 5B is a cut-away view showing catheter 60 positioned within connection element 25, with distal end 62 of catheter exiting attachment element and within reservoir 40.

Figure 6A:
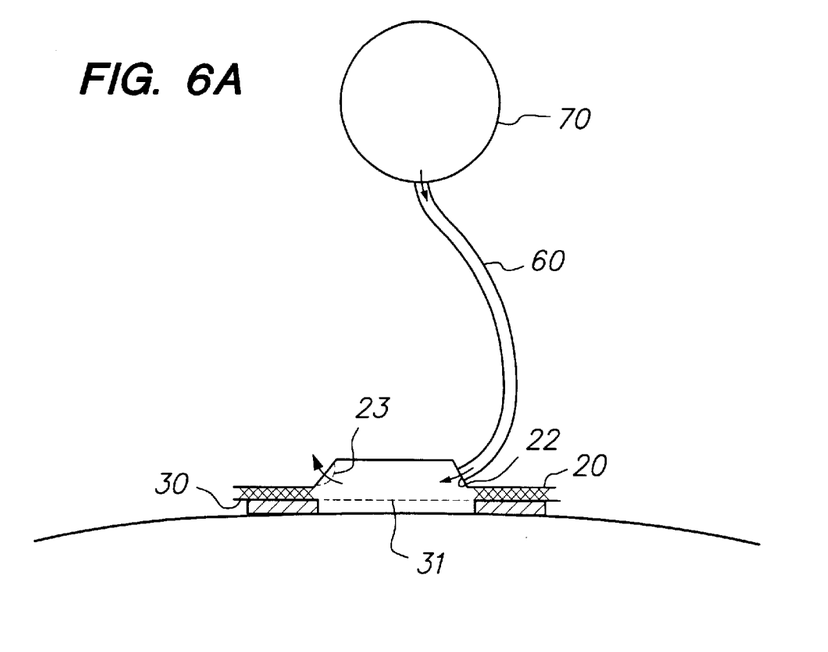
FIGS. 6A and 6B depict additional exemplary embodiments of a drug delivery system of the invention.
Figure 6B:
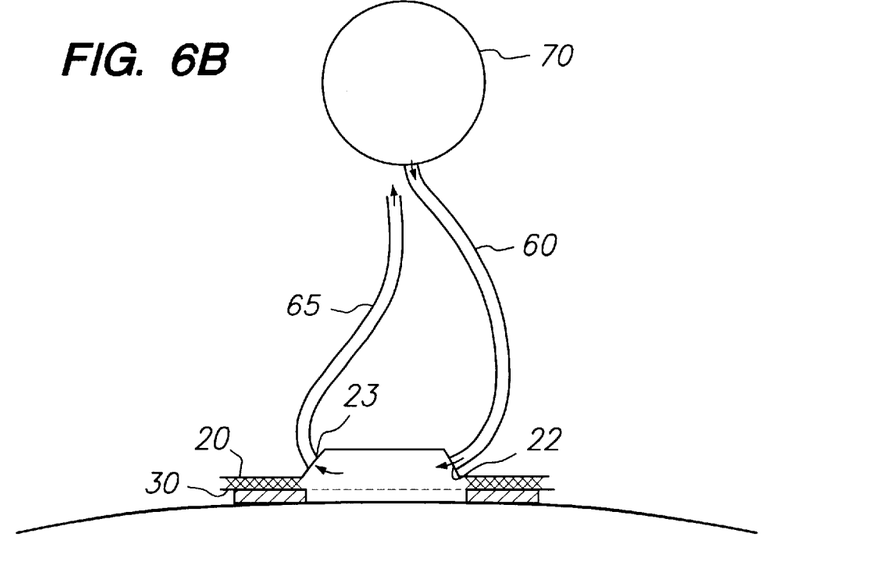

FIGS. 6A and 6B depict additional exemplary non-limiting embodiments of the drug delivery system of the invention. FIGS. 6A and 6B depict a continuous flow, or circulating, system. In FIG. 6A, drug formulation enters drug reservoir 40 from catheter 60 through inlet 22 in patch first layer 20. Drug then exits from drug permeable portion 31 of patch second layer 30. To maintain the drug concentration at a substantially constant level in the reservoir, formulation substantially depleted of drug exits drug reservoir from an outlet 23 in the first layer. Direction of solvent flow is indicated by arrows. In the embodiment shown in FIG. 6A, formulation substantially depleted of drug exits the outlet directly into the body of the subject (e.g., peritoneal cavity). FIG. 6B depicts a variation in which formulation substantially depleted of drug exits the outlet 23, flows through an outlet tube 65, and out of the body. Direction of solvent flow is indicated by arrows.

Figure 7A:
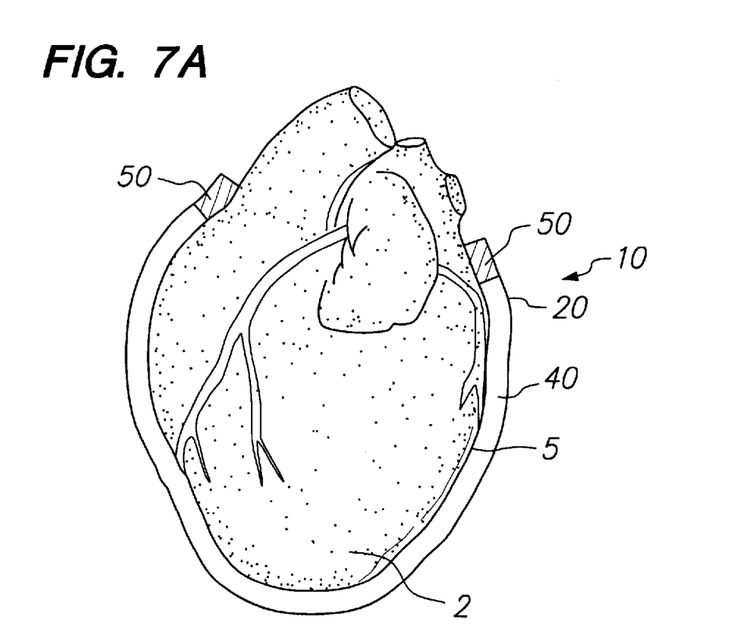
FIGS. 7A and 7B depict exemplary embodiments of an implantable patch of the invention, positioned on the pericardium for delivery of drug.
Figure 7B:
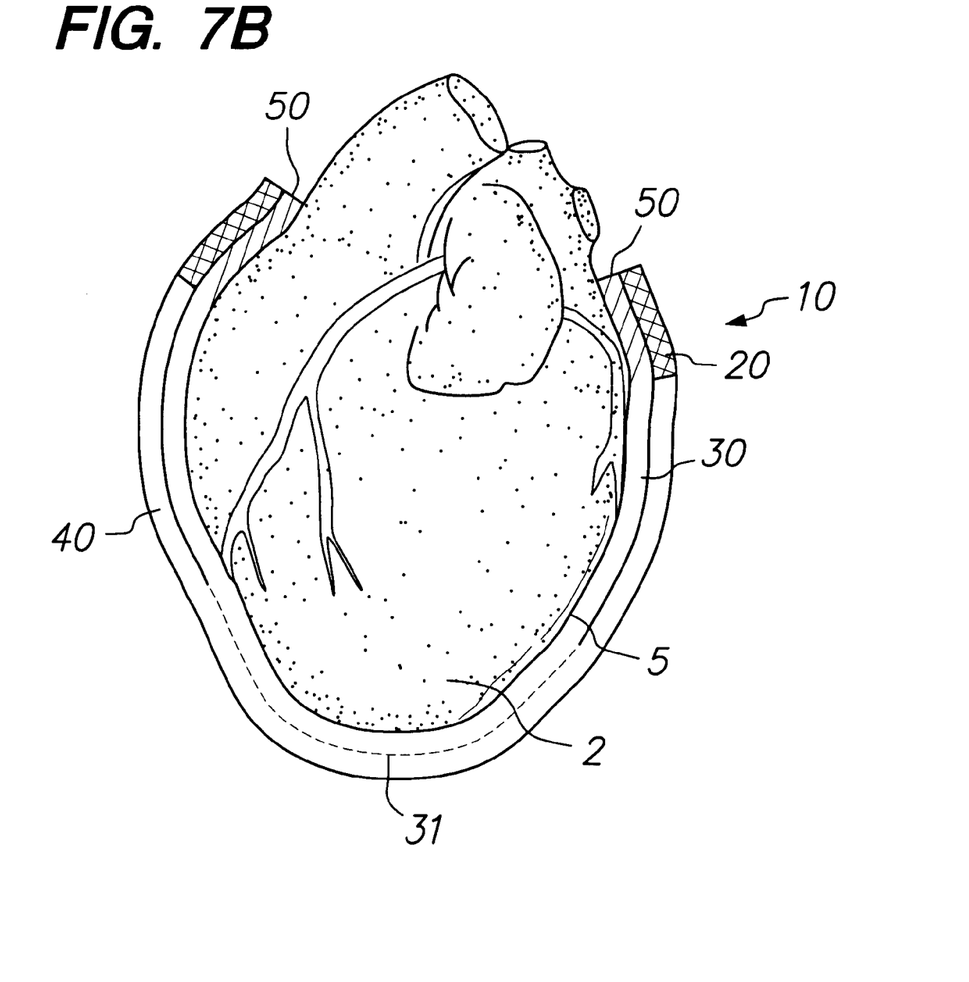

FIGS. 7A and 7B depict additional exemplary non-limiting embodiments of the invention. FIG. 7A depicts a patch 10 with first layer 20 positioned on the outer surface 5 of an organ 2, e.g., a heart. In this exemplary embodiment, the attachment element 50 is generally annular in configuration, and is positioned such that the first layer 20 forms a sack around the organ. The first layer is affixed to the outer surface of the organ by attachment element 50, positioned and configured such that the first layer substantially surrounds the organ. A reservoir 40 is formed by the first layer 20 and the outer surface of the organ. FIG. 7B shows a further exemplary embodiment in which a patch 10 comprises a first layer 20 and a second layer 30 positioned on the outer surface 5 of an organ 2. In this exemplary embodiment, the attachment element 50 is generally annular, and a reservoir 40 is formed between the first and second layers. First and second layers are attached to one another (as indicated by cross-hatching) except for the portions forming the reservoir. In this exemplary embodiment, the second layer 30 comprises a drug-permeable portion 31. These embodiments are particularly useful when the membrane surrounding the organ. (e.g., a pericardial sac) is not intact.

Additional Embodiments

In an additional embodiment, the patch of the invention comprises a fluid imbibing pump for controlled delivery to the organ surface, as described in U.S. Pat. No. 4,655,766.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An implantable drug delivery patch for delivery of drug to an internal organ of a subject, comprising:

a) a first layer, wherein the first layer is substantially impermeable to a drug;

b) a second layer attached to the first layer so as to form a reservoir between the first and second layers, the second layer comprising a portion which is permeable to a drug, wherein, upon placement of the patch on the outer surface of the internal organ, the second layer is disposed between the first layer and the organ surface, and wherein the second layer comprises a membrane which provides for controlled rate of release of drug from the reservoir;

wherein at least one layer selected from the group consisting of the first layer and the second layer comprises an adhesive portion that acts as an attachment element adapted for affixing the drug delivery patch to the outer surface of the organ.

2. The patch according to claim 1, wherein said first layer is continuous with said second layer.

3. The patch according to claim 1, wherein the reservoir is fillable after placement on an organ.

4. The patch according to claim 1, wherein the patch is pre-filled with a pharmaceutical formulation comprising a therapeutic drug.

5. The patch according to claim 4, wherein the pharmaceutical formulation further comprises a penetration enhancer.

6. The patch according to claim 4, wherein the formulation further comprises a gel which provides for a controlled rate of release of drug from the reservoir.

7. The patch according to claim 1, wherein the drug-permeable portion has an area in the range of about 0.5 $cm^2$ to about 10 $cm^2$.

8. The patch according to claim 1, further comprising a third layer, wherein said third layer is a strippable release liner adjacent the second layer, is substantially drug-impermeable, and is adapted to be stripped off of the patch before the patch is affixed to the organ surface.

9. The patch according to claim 1 wherein the reservoir is refillable.

10. The patch according to claim 9, further comprising a connection element for connecting a device for refilling the reservoir.

11. The patch according to claim 1, wherein the patch is biodegradable.

12. The patch according to claim 1, wherein the patch is sized for use in delivery to an internal organ selected from the group consisting of heart, liver, pancreas, prostate, ovary, uterus, brain, stomach, intestine, lung, kidney, a lymph node, and a joint capsule.

13. An implantable drug delivery patch for delivery of drug to an internal organ of a subject, comprising:

a) a first layer adapted to be positioned on an outer surface of an internal organ so as to form a reservoir between said first layer and said organ outer surface, wherein said first layer is substantially impermeable to a drug; and b) an attachment element adapted for affixing said patch to the outer surface of the organ, wherein said patch is configured so as to form a sack which substantially surrounds the organ.

14. The drug delivery patch according to claim 13, further comprising a second layer attached to the first layer so as to form a reservoir between the first and second layers, the second layer comprising a portion which is permeable to a drug, wherein, upon placement of the patch on the outer surface of the organ, the second layer is disposed between the first layer and the organ surface.

15. The patch according to claim 14, wherein said first layer is continuous with said second layer.

16. The patch according to claim 13, wherein the reservoir is refillable.

17. The patch according to claim 16, further comprising a connection element for connecting a device for refilling the reservoir.

18. A drug delivery system, comprising:
    a) an implantable drug delivery patch according to claim 1, wherein said patch further comprises an inlet in the first layer;
    b) a catheter having a proximal end and a distal end, the distal end operably attached to the inlet; and
    c) a drug delivery device operably attached to the proximal end of the catheter.

19. The drug delivery system of claim 18, wherein the drug delivery device is a convective device.

20. The drug delivery system of claim 19, wherein the convective device is selected from the group consisting of an electromechanical pump, an electroosmotic pump, a hydrolytic system, a piezoelectric pump, an elastomeric system, a vapor pressure pump, and an electrolytic pump.

21. The drug delivery system of claim 19, wherein the convective device is an osmotic pump.

22. The drug delivery system of claim 18, wherein the drug delivery device is a diffusion system.

23. The drug delivery system of claim 18, further comprising an outlet in said first layer, wherein formulation substantially depleted of drug exits said outlet, and wherein formulation comprising drug enters said inlet, thereby forming a circulating drug delivery system.

24. A drug delivery system, comprising:
    a) an implantable drug delivery patch according to claim 13, wherein said patch further comprises an inlet in the first layer;
    b) a cathether having a proximal end and a distal end, the distal end operably attached to the inlet; and
    c) a drug delivery device operably attached to the proximal end of the catheter.

25. A method of treating an individual having a cardiac condition, comprising delivering a therapeutic agent to the individual using a drug delivery patch according to claim 1, thereby treating the cardiac condition.

26. A method of treating an individual having a cardiac condition, comprising delivering a therapeutic agent to the individual using a drug delivery system according to claim 18, thereby treating the cardiac condition.

27. The patch according to claim 1 wherein the organ to which drug is delivered is the heart.

28. The patch of claim 27 wherein the drug is selected from the group consisting of: anti-arrhythmia agents, angiogenic agents, anti-inflammatory agents, angiogenic factors and calcium channel blockers.

29. The patch of claim 27, wherein the drug is delivered at a rate of between about 0.01 micrograms per hour and 200 micrograms per hour.

30. The patch of claim 27, wherein the drug is delivered in a formulation, and wherein the formulation is delivered at a volume rate that is substantially constant.

31. The patch of claim 30, wherein the drug is delivered in a formulation, and where the formulation is delivered at a volume rate of about 0.04 to about 10 microliters per day.

32. The patch of claim 27 wherein said placement of the patch is on the pericardium of the heart, wherein the drug enters and crosses the pericardium, then enters the pericardial fluid and then enters the cardiac tissue.

33. The patch of claim 27 wherein the second layer comprises a microporous membrane.

* * * * *